(12) United States Patent
Dartey et al.

(10) Patent No.: US 6,875,443 B2
(45) Date of Patent: Apr. 5, 2005

(54) ENCAPSULATED LONG CHAIN ALCOHOLS

(75) Inventors: Clemence K. Dartey, North Wales, PA (US); Thomas E. Sox, Ambler, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 39 days.

(21) Appl. No.: 10/023,177

(22) Filed: Dec. 17, 2001

(65) Prior Publication Data

US 2002/0076432 A1 Jun. 20, 2002

Related U.S. Application Data

(62) Division of application No. 09/461,592, filed on Dec. 15, 1999, now Pat. No. 6,355,274.

(51) Int. Cl.$^7$ ............................. A61K 9/14; A61K 9/16; A61K 47/00; A23L 1/22; A23L 1/216
(52) U.S. Cl. ...................... 424/439; 424/489; 424/490; 424/493; 424/494; 424/495; 426/89; 426/96; 426/97; 426/98; 426/99
(58) Field of Search ................................ 424/439, 489, 424/490, 493, 494, 495; 426/89, 96, 97, 98, 99

(56) References Cited

U.S. PATENT DOCUMENTS

| | | | |
|---|---|---|---|
| 3,031,376 A | | 4/1962 | Levin et al. |
| 3,881,005 A | * | 4/1975 | Thakkar et al. .............. 424/238 |
| 4,391,732 A | | 7/1983 | Lundmark |
| 4,507,327 A | * | 3/1985 | Ueda ........................... 426/276 |
| 5,271,881 A | * | 12/1993 | Redding, Jr. ................. 264/432 |
| 5,460,756 A | | 10/1995 | Redding, Jr. et al. |
| 5,502,045 A | | 3/1996 | Miettinen et al. |
| 5,663,156 A | | 9/1997 | Granja et al. |
| 5,770,749 A | | 6/1998 | Kutney et al. |
| 5,856,316 A | * | 1/1999 | Laguna Granja et al. ... 514/164 |
| 5,869,708 A | | 2/1999 | Das et al. |
| 5,892,068 A | | 4/1999 | Higgins, III |
| 5,952,393 A | * | 9/1999 | Sorkin, Jr. ................... 514/729 |
| 5,961,707 A | * | 10/1999 | Mothes et al. ........... 106/205.7 |
| 6,123,978 A | | 9/2000 | Dartey et al. |
| 6,355,274 B1 | | 3/2002 | Dartey et al. |

FOREIGN PATENT DOCUMENTS

| | | |
|---|---|---|
| EP | 0 801 904 A1 | 10/1997 |
| EP | 0 897 671 A1 | 2/1999 |
| EP | 0901804 A1 | 3/1999 |
| EP | 1 108 363 A1 | 6/2001 |
| EP | 1 108 364 A2 | 6/2001 |
| JP | 51 1113 * | 12/1968 |
| JP | 62099323 | 5/1987 |
| JP | 61058536 | 3/1988 |
| JP | 83133969 | 6/1988 |
| WO | WO 94/07830 A1 | 4/1994 |
| WO | WO 98/19556 * | 5/1998 |
| WO | WO 98/19556 A1 | 5/1998 |
| WO | WO 98/47385 A1 | 10/1998 |
| WO | WO 98/47385 * | 10/1998 |
| WO | WO 99/40922 A1 | 8/1999 |
| WO | WO 00/45648 A1 | 8/2000 |
| WO | WO 01/32031 A2 | 5/2001 |

OTHER PUBLICATIONS

Sho et al., Effects of Okinawan Sugar Cane Wax and Fatty Alcohol on Serum and Liver Lipids in the Rat; J. Nutr. Sci. Vitaminol., 30, pp 553–559, 1984.*

Miltenberger, K.H.; Gas Chromatographic Study of Natural Waxes; from Wachs, 2(12) (1970), pp. 736–742.

Sho, H. et al.; Effects of Okinawan Sugar Cane Wax and Fatty Alcohol on Serum and Liver Lipids in the Rat; J. Nutr. Sci. Vitaminol., 30, pp. 553–559, 1984.

Patent Abstracts of Japan—JP 02150260 Nippon Oil & Fats Co. Ltd. Jun. 8, 1990.

* cited by examiner

*Primary Examiner*—Thurman K. Page
*Assistant Examiner*—S. Tran

(57) ABSTRACT

The present invention is directed to the encapsulation of long chain alcohols, $C_{20}$–$C_{36}$, in various materials including polymers and waxes. Through the proper selection of the polymer the encapsulated long chain alcohol can be advantageously added to foods such as margarines, salad dressings and the like.

6 Claims, No Drawings

ENCAPSULATED LONG CHAIN ALCOHOLS

RELATED APPLICATIONS

This application is a divisional of prior application Ser. No. 09/461,592, filed Dec. 15, 1999, which issued as U.S. Pat. No. 6,355,274 B1 on Mar. 12, 2002. This application is being concurrently filed with two additional applications. These related applications are entitled Long Chain Alcohols Provided in Edible Oils, U.S. Ser. No. 09/461,887 and Long Chain Alcohols Admixed in Sterol Compounds, U.S. Ser. No. 09/461,607, the contents of these applications incorporated by reference as if set forth in their entirety.

FIELD OF THE INVENTION

The present invention relates to the incorporation of long chain alcohol substances, more specifically the present invention relates to the encapsulation of long chain alcohols so as to more readily incorporate them into foods.

BACKGROUND OF THE INVENTION

Long chain alcohols, including policosanol, are therapeutically useful materials with efficacy in lowering cholesterol or blood lipids, inhibiting platelet aggregation and improving stamina. Therefore, the incorporation of long chain alcohols such as policosanol in various foods is desirable.

Incorporation of policosanol into high fat or fat-continuous emulsion systems such margarine and margarine spreads is complicated by the functional properties of policosanol. In particular, incorporation of policosanol into a margarine oil system containing a diglyceride and a phospholipid causes an increase in the hardness of a margarine type product as disclosed in WO 98/47385. In addition, EP 0901804 discloses that the incorporation of a natural long chain alcohol in a fat continuous system reduces the viscosity and yield values of confectionery products.

Despite these disclosures there is still an ongoing need to be able to add long chain alcohols to foods in a manner that the long chain alcohol will be easily formulated, will remain stable during storage, and will not adversely affect the properties of the food.

SUMMARY OF THE INVENTION

The present invention provides comestibles containing a physiologically effective amount of a long chain alcohol, said long chain alcohol encapsulated by a polymer, waxes and plasticizers. The present invention also provides methods for providing these comestibles. The present invention also provides methods for lowering cholesterol in a vertebrate by administering these long chain alcohols in comestible form.

DETAILED DESCRIPTION OF THE INVENTION

The present invention is directed to the encapsulation of long chain alcohols and the incorporation of these alcohols into food products. By long chain alcohols, it is understood to mean both saturated and unsaturated alcohols of $C_{20}$ and above, primarily from $C_{20}$ to $C_{36}$. As used herein, long chain alcohols are understood to be those materials which contain more than about 90 weight percent $C_{20}$ or longer, primarily aliphatic alcohol materials. For the greatest health benefit it is preferred that the long chain alcohols be greater than 50 percent, octacosanol ($C_{28}$), preferably more than 65 percent, more preferably greater than about 70 weight percent octacosanol. As used herein policosanol is understood to be a mixture of long chain alcohols ranging from $C_{20}$ to $C_{36}$ with greater than 50 weight percent $C_{28}$, preferably greater than 65 weight percent $C_{28}$. Common distribution and concentration ranges of the various components of policosanol are disclosed in U.S. Pat. No. 5,856,316, hereby incorporated by reference as if set forth in its entirety. The most preferred source of long chain alcohols is waxes, particularly sugar cane wax. The long chain alcohols can also be synthesized using techniques known in the art.

The level of long chain alcohol in the food product is determined by serving size. It is desirable to provide in a single serving an effective amount of the long chain alcohol to derive the desired physiological benefits, such as reduced platelet aggregation, reduced lipid and cholesterol levels and the like. Typically the level of the long chain alcohol is from about 0.1 to about 100 milligrams/serving; preferably from about 0.5 to about 20 milligrams/serving and most preferably from about 2 to about 10 milligrams/ serving.

Encapsulation as used herein is understood to mean a protective barrier to limit, if not prevent, the dissolution or dispersion into the liquid phase into which it is incorporated. The present invention contemplates surrounding the long chain alcohol by a coating of polymer. Other embodiments include multiple particles of the long chain alcohol in a matrix form surrounded by a coating. Other embodiments are possible without departing from the scope of the present invention.

There are many foods into which the encapsulated long chain alcohols are incorporated, including but not limited to margarine, spreads, salad dressings, cookies, confectionery products, creams, cheeses, oils, gums, candy and the like.

Numerous technologies practiced in the food and pharmaceutical industries are suitable for coating the long chain alcohol, and in a preferred embodiment for coating policosanol. These technologies are also suitable for coating long chain alcohols of $C_{20}$ to $C_{36}$, as well as various blends of the alcohols. The particular coatings used are intended to prevent the dissolution or dispersion of the long chain alcohol into the food or beverage product into which it is incorporated. This prevents the aforementioned physical effects of the long chain alcohol on the food or beverage product. Additionally, the coatings are intended to dissolve or disintegrate at some point in the gastrointestinal tract so that the long chain alcohol can provide physiological benefits.

Preferred methods for forming the encapsulated long chain alcohol particles are found in U.S. Pat. Nos. 5,271,881 and 5,460,756, both patents herein incorporated by reference. These patents disclose the use of a coacervation device which provides a pressure drop across an opening resulting in a coating or the mixing of coatings which would encapsulate the long chain alcohol. These patents also disclose a method for entrapping liquids in a lipid matrix by melting the lipid, adding the liquid to the melted wax, placing the admixture where it may be subjected to the action of a piston, subjecting the liquid/lipid to at least one stroke of the piston and allowing the lipid to solidify.

In an alternative process, a coating, preferably a combination of hydroxypropylmethylcellulose/polyethylene glycol are supplied in a defined ratio, preferably in a 9:1 weight ratio dissolved in an ethanol/water mixture. The coating is applied onto long chain alcohol, such as policosanol (Garuda International, Santa Cruz, Calif.) using air fluidized bed techniques employed in the pharmaceutical arts.

It is preferred that the long chain alcohols of the present invention are of a particle size less than about 35 microns, preferably from about 10 to about 30 microns and most preferably from about 15 to about 25 microns. Particle size reduction of the long chain alcohol is carried out through techniques that are known in the art, including but not limited to grindings, hammermills, cryogenic grinding, spray congealing, and the like. Particles in this size range minimize any aesthetic problems of coarseness or grittiness in the product, but are sufficiently large so that the mass of coating applied does not constitute a disproportionately large portion of the particle.

The encapsulating coating materials of the present invention are selected from the group consisting of food grade acceptable materials including waxes, natural polymers, synthetic polymers and synthetic elastomers. Waxes include glycerin tristearate, distearate, canola wax, soya flakes, rapeseed wax, glyceryl cotton flakes, castor wax, beeswax, carnauba wax, candelella wax and the like.

Suitable polymers include naturally derived celluose derivatives such as cellulose acetate, cellulose acetate butyrate, cellulose acetate phthalate, hydroxypropylcellulose, hydroxypropylmethylcellulose, methylcellulose, cellulose triacetate and ethylcellulose. Other synthetic polymers include polyvinylpyrrolidone, methylaminoethylmethacrylate and neutral methacrylic acid esters, 2-vinyl pyrridine styrene copolymer, polyoxyethylene, and polyoxypropylene. Other natural polymers include arabinogalactan, alginate, zein, xanthan gum, gum arabic, gelatin, and tragacanth gum. Mixtures of the above-described coating materials are also contemplated by the present invention.

The weight ratios of the long chain alcohol to encapsulating material can vary broadly from about 1:4 to about 10:1. Preferably the weight ratio of the long chain alcohol to the encapsulating material is greater than 60:40; more preferably greater than about 70:30 and in a highly preferred embodiment greater than about 80:20. The encapsulating material can be a single material or a mixture of coatings. In a highly preferred embodiment multiple coatings can be sequentially applied to the long chain alcohol. For example, an elastomeric coating can be the outermost coating to protect an inner coating which could be a blend of hydrophilic and hydrophobic materials. The blending of the encapsulating material would be dependent on the food to which the long chain alcohol is incorporated.

Varying the encapsulating materials allows the long chain alcohol to be more readily suspended in hydrophilic or hydrophobic systems. In another embodiment of the invention, both hydrophilic and hydrophobic encapsulating materials can be applied to the long chain alcohol. This will provide a long chain alcohol that is found throughout the food products that contain both lipid and aqueous regions such as margarine. Other coating materials can be applied such as an enteric coating such as cellulose acetate phthalate, polyvinylacetate phthalate, hydroxypropyl methylcellulose phthalate, and EUDRAGIT L-30-D (anionic polymers based on methacrylic acid and methacrylic acid esters commercially available from Rohm Pharma GmbH, Germany) and the like; as well as reverse enteric coatings such as EUDRAGIT E-100 (methylaminoethyl-methacrylate and neutral methacrylic acid esters available from Rohm Pharma GmbH, Germany) and the like.

In a preferred embodiment, policosanol is coated with a lipophilic material such as polyvinylpyrridonne and is dispersed and suspended in the oil phase while policosanol coated with a hydrophilic material such as hydroxypropyl-methylcellulose is dispersed and suspended in the aqueous phase in a margarine product.

In a highly preferred embodiment, ingredients which have desirable physiological actions are also added to the food. Such materials include soy, vitamins, minerals and the like. In a highly preferred embodiment, a second cholesterol-lowering ingredient, such as oryzanols, stanols, sterols, stanol esters and sterol esters, is provided in an effective amount in the food. A particularly preferred sterol ester is β-sitosterol. These materials are well known in the art and are disclosed in U.S. Pat. Nos. 3,881,005; 5,502,045; 5,869,708 and 5,892,068. The level of sterol or stanol used in the present invention should be sufficient to provide an amount effective to lower cholesterol in a human when consumed on a routine basis. Typically the sterol level is from about 0.1 to about 20, preferably from about 0.3 to 10, and most preferably from about 0.5 to about 4 grams per serving.

If the stanols/sterols are present, these materials preferably should be melted and blended with the coated particles of long chain alcohols and in a preferred embodiment with suitable ingredients before the long chain alcohol material is dispersed in the oil phase. Suitable oil sources include sunflower, safflower, corn, soybean, canola mixtures of these oils and the like.

While particle size of the long chain alcohol can vary widely, a preferred embodiment is to have the long chain alcohol to be less than about 200 microns in diameter. A highly preferred embodiment is to produce stable microencapsulated policosanol or coated microparticles of the long chain alcohol, preferably policosanol, having a diameter of less than 30 microns, preferably from about 15 to about 25 microns in diameter, that are dispersible in lipid or aqueous emulsion systems of foods.

It is the intention of the invention to produce coated policosanol particles that would not dissolve when dispersed in an oil phase or aqueous phase. Since the encapsulated policosanol is not dissolved in the oil phase, it is prevented from inducing any changes in the consistency or physical qualities of a finished product. The sizes of the particles within the coated policosanol material were limited to less than 30 microns to induce a creamy mouthfeel.

The encapsulated long chain alcohols can be advantageously incorporated into various food, beverage and pharmaceutical forms. Among those products include salad dressings, margarines, mayonnaise dressings, nutrition bars, beverages, juices, ice cream, yogurts, frozen yogurts, non-dairy creamers, cheese spreads, cheeses, milk products, confectioneries, chocolate-containing products such as cakes and cookies. Other forms include pharmaceutical preparations such as tablets, soft gelatin capsules, suspensions, emulsions and the like. The encapsulated long chain alcohols of the present invention are advantageously used to lower the cholesterol level of vertebrates, including mammals, amphibians, reptiles and the like. Most preferably the long chain alcohol is administered to a human to lower the cholesterol level of a human.

The following are provided as specific embodiments of the present invention. Other modifications of this invention will be readily apparent to those skilled in the arts without departing from the scope of this invention. As used herein all percentages are weight percent, mg is understood to be milligrams and g is understood to be grams. The supplier of the materials used in the examples is provided in parenthesis. The microencapsulated particles used in Examples 1–5 were prepared from policosonal (CHOLESSTANOL, Garuda International) and hydroxypropylmethylcellulose (HPMC). The particles were prepared by Delta Foods, Aston, Pa., by the methodology described in U.S. Pat. No. 5,271,881.

EXAMPLE 1

This example describes the application of microencapsulated policosanol in a margarine spread product. The margarine spreads were prepared on the bench top. The soybean oil, partially hydrogenated soybean oil, canola oil, stanol esters if present in the formula, monoglycerides, lecithin and hexaglycerol distearate were mixed together in a two liter stainless steel container. The container was heated in a water bath to about 140° F. to melt the solid fats in the mixture. After removing the container from the water bath, the flavor, vitamin blend and carotene color were added and mixed in the liquid fat. After cooling the oil to about 130° F., the policosanol material was added slowly and dispersed in the oil blend using a LIGHTENING mixer. The water phase was prepared by dissolving the salt, citric acid, ethylenediaminetetra-acetic acid (EDTA) and potassium sorbate in the water. The margarine emulsion was prepared by mixing the hot oil phase at approximately 130° F. at high speed and adding the aqueous phase slowly to it. While blending the emulsion at high speed, the container was chilled in a salted ice bath until the emulsion firmed up into a soft margarine consistency. The container was removed from the ice bath and the finished margarine product was packed into plastic tubs and stored overnight in a refrigerator. The results showed that the bench top process produced a margarine product similar in characteristics to margarine products prepared in the pilot plant using a scrape surface heat exchanger.

TABLE 1

Cholesterol Lowering Margarine Spreads Containing Microencapsulated Policosanol with or without Stanol Esters.

| Ingredients | Formula 1 Weight (g) | Formula 2 Weight (g) |
| --- | --- | --- |
| Oil Phase | | |
| Liquid Soybean Oil | 111.381 | 117.923 |
| Partially Hydrogenated Soybean Oil | 175.000 | 110.000 |
| Liquid Canola Oil | 325.000 | 300.000 |
| Stanol Esters | 0.000 | 215.500 |
| Monoglycerides | 4.000 | 3.000 |
| Lecithin | 3.000 | 2.000 |
| Hexaglycerol Distearate 6-2-S, (Polyaldo) | 0.500 | 1.000 |
| Artificial Butter Flavor #598.769/AH (Firmenich) | 0.700 | 0.700 |
| Vitamin A & D Blend | 0.063 | 0.063 |
| Beta-Carotene, 30% | 0.015 | 0.015 |
| Microencapsulated Policosanol with 20% Coating Material | 0.855 | 0.855 |
| Aqueous Phase | | |
| Water | 358.341 | 227.799 |
| Salt | 20.000 | 20.000 |
| Citric Acid | 0.075 | 0.075 |
| Calcium Disodium EDTA | 0.070 | 0.070 |
| Potassium Sorbate | 1.000 | 1.000 |
| TOTAL | 1000.000 | 1000.000 |

(Formula 1 contained approximately, 5 g policosanol per 8 grams of the margarine spread while Formula 2 contained approximately, 5 mg policosanol plus approximately, 1.7 g stanol esters per 8 grams of the margarine spread).

The margarines containing microparticulated policosanol produced by the previously described process were similar in organoleptic and physical properties to margarines made without microencapsulated policosanol.

EXAMPLE 2

This example describes the application of microencapsulated policosanol in typical ranch dressings. The coated policosanol with 80 percent active policosanol material was dispersed in the oil phase compositions.

TABLE 2

Cholesterol-Lowering Ranch Dressing Containing Stanol Esters and or Microencapsulated Policosanol.

| Ingredients | Ranch Dressing with Coated Policosanol Weight (g) | Ranch Dressing with Coated Policosanol plus Stanol Esters Weight (g) |
| --- | --- | --- |
| Soybean Salad Oil | 551.34 | 480.00 |
| Vinegar | 84.00 | 84.00 |
| Stanol Esters | 0 | 71.34 |
| Sugar, Fine Granulated | 58.80 | 58.80 |
| Ranch Seasoning | 50.40 | 50.40 |
| Cultured Buttermilk Solids (Armour Co) | 19.20 | 19.20 |
| Salt | 8.40 | 8.40 |
| CAPROL ET (A. C. Humko) | 7.44 | 7.44 |
| Egg Yolk, Liquid, 10% Salt | 4.32 | 4.32 |
| KELTROL T Xanthan Gum (Kelco) | 4.20 | 4.20 |
| Polysorbate 60 | 3.00 | 3.00 |
| Lemon Juice Concentrate | 3.00 | 3.00 |
| Propylene Glycol Alginate (Kelco) | 2.10 | 2.10 |
| Polysorbate 80, TWEEN 80 | 1.92 | 1.92 |
| Titanium Dioxide | 1.68 | 1.68 |
| Potassium Sorbate | 0.96 | 0.96 |
| Sodium Benzoate | 0.96 | 0.96 |
| Microencapsulated Policosanol, 20% Coating Material | 0.28 | 0.28 |
| Vitamin E Acetate, (Roche) | 0.22 | 0.22 |
| DL-Alpha-Tocopherol | 0.10 | 0.10 |
| Calcium Disodium EDTA | 0.07 | 0.07 |
| Paprika Oleoresin | 0.02 | 0.02 |
| Water | 397.59 | 397.59 |
| Total | 1200.00 | 1200.00 |

The ranch dressings were produced in the laboratory using a POWERGEN homogenizer as the mixing unit. The preservatives, sodium benzoate and potassium sorbate and EDTA were dissolved in the water. A mixture of the two hydrocolloid gums, xanthan gum and propylene glycol alginate, was dispersed in a portion of the vegetable oil, (1 part gum mixture in about 2–5 parts of the oil). The gum dispersion was blended and hydrated in the water at 8,000 rpm for 5 minutes. After blending in the vinegar and lemon juice, the sugar, buttermilk solids, ranch seasoning, salt and titanium dioxide were added and blended at 12,000 rpm for 5 minutes. The polysorbates, 60 and 80, were melted together and added with the liquid egg yolk and blended at 12,000 rpm for 60 seconds. CAPROL ET was added to the salad oil and the stanol esters, if present. The mixture was heated to melt the CAPROL ET and stanol esters. The oil blend was cooled to about 120° F. After adding and mixing in vitamin E, tocopherol and color, the encapsulated policosanol material was mixed and dispersed uniformly in the oil. While blending the aqueous phase at 14,000 rpm, the policosanol-enriched oil was added slowly to prepare the ranch dressing. The finished dressing was filled into bottles.

EXAMPLE 3

This example describes the application of microencapsulated policosanol in a typical light ranch dressing. The encapsulated policosanol was dispersed in the oil phase and used to prepare the light ranch dressing emulsion.

TABLE 3

The application of microencapsulated policosanol in a typical light ranch dressing formulation.

| Ingredients | Ranch Dressing with Coated Policosanol Weight (g) |
|---|---|
| Soybean Salad Oil | 250.00 |
| Vinegar | 80.00 |
| Sugar, Fine Granulated | 46.00 |
| Ranch Seasoning | 60.00 |
| OPTAMIST, Modified Food Starch, (Opta Foods) | 15.00 |
| Cultured Buttermilk Solids, (Armour Co.) | 14.00 |
| Salt | 6.00 |
| Egg Yolk, Liquid, 10% Salt | 3.60 |
| KELTROL T Xanthan Gum, (Kelco) | 2.24 |
| Polysorbate 60 | 3.00 |
| Lemon Juice Concentrate, 400 GPL | 3.60 |
| Propylene Glycol Alginate, Kelco | 1.20 |
| Polysorbate 80, TWEEN 80 | 1.60 |
| Titanium Dioxide | 2.00 |
| Potassium Sorbate | 0.50 |
| Sodium Benzoate | 0.50 |
| Onion Powder | 0.40 |
| Microencapsulated Policosanol, 20% Coating | 0.24 |
| Vitamin E Acetate, Roche | 0.22 |
| DL-Alpha-Tocopherol | 0.10 |
| Calcium Disodium EDTA | 0.07 |
| Paprika Oleoresin 1000ASTA | 0.02 |
| Water | 509.71 |
| Total | 1000.00 |

The process for the light ranch dressing was similar to the process outlined above for a typical ranch dressing.

EXAMPLE 4

This example describes the application of microencapsulated policosanol to prepare a two-phase or a separating-type Italian dressing. In processing the two-phase Italian dressing, the encapsulated policosanol was dispersed in one experiment in the oil phase and in another experiment, it was dispersed in the aqueous phase. The results indicated that for a two-phase Italian dressing, microencapsulated policosanol could be applied in the oil phase or in the aqueous phase.

TABLE 4

Two-Phase Italian Dressing Containing Microencapsulated Policosanol.

| Ingredients | Weight (g) |
|---|---|
| Soybean Salad Oil | 440.00 |
| Microencapsulated Policosanol, 20% Coating | 0.24 |
| Cidar Vinegar, 50 Grain | 280.00 |
| Salt | 10.00 |
| Lemon Juice Concentrate, 400 GPL | 50.00 |
| KELTROL T Xanthan Gum, (Kelco) | 0.15 |
| Oregano | 1.00 |
| Minced Garlic | 7.50 |
| Minced Onion | 7.50 |
| Chopped Sweet Red Pepper | 5.00 |
| Whole Italian Seasoning | 3.00 |
| Parsley Flakes | 3.00 |
| Crushed Red Pepper | 2.00 |
| Celery Seed | 0.80 |
| Black Pepper | 0.80 |
| Water | 189.01 |
| Total | 1000.00 |

The two-phase Italian dressing was prepared by either dispersing the policosanol material in the oil or in the water using a Lightening mixer. The dry ingredients including xanthan gum, salt, oregano, garlic, onion, peppers, parsley and celery seeds were mixed together. The mixture was blended gently in the water solution containing vinegar and lemon juice. After shaking the aqueous phase composition to disperse the particles evenly, the composition was poured into 8 ounce dressing bottles, filling about 56% capacities of the bottles. The bottles were then topped with the salad oil or with the policosanol-enriched salad oil.

EXAMPLE 5

This example describes the application of microencapsulated policosanol in a vegetable oil such as olive oil. The microencapsulated policosanol was dispersed and suspended uniformly in the olive oil. The policosanol remained stable and uniformly suspended in the oil during prolonged storage.

TABLE 5

Policosanol-Enriched Olive Oil.

| Ingredient | Weight (g) |
|---|---|
| Olive Oil | 999.49 |
| Microencapsulated Policosanol, 20% Coating | 0.51 |
| Total | 1000.00 |

The microencapsulated policosanol was blended at high speed to disperse and suspend uniformly in the olive oil. The policosanol dosage was 5 mg active per 13.5 g olive oil. The policosanol-enriched olive oil sample prepared appeared slightly cloudy but it remained stable during prolonged storage at room temperature.

In a comparative example, policosanol was melted and dissolved in a vegetable oil heated to about 160–180° F. After cooling the policosanol-enriched oil and storing it at room temperature, the appearance of the oil changed. It became translucent in nature. During further storage of the oil at room temperature, syneresis occurred and this finally resulted in a gel-like precipitate and a clear oil layer. In contrast as described in the earlier example, the application of microencapsulated policosanol in an olive oil did not induce a gel-like precipitate. The encapsulated policosanol particles remained suspended uniformly in an olive oil during prolonged storage.

EXAMPLE 6

Octacosanol was coated with a hydroxypropylmethylcellulose (HPMC) and polyethylene glycol (PEG) solution to produce a coated particle.

HPMC (Pharmacoat 606) 11.11 g and PEG 8000 (11.11 g) were dissolved in ethanol (156 g) and water (44 g) to produce a solution with a 50:50 polymer weight ratio containing 10 weight percent polymer solids. Octacosanol (200 g) was charged into a Glatt GPCG-3 rotor coater. The polymer solution sprayed onto the fluidized material under the following conditions:

| | |
|---|---|
| inlet air temperature | 60° C. |
| product temperature | 23–32° C. |
| inlet air volume | 40 cubic feet per minute |
| spray rate | 12 g/minute |
| nozzle size | 1.2 millimeter |
| rotor speed setting | 720 |
| filter shake | ·4 seconds per every 30 seconds. |

Before encapsulation, the octacosanol had a average particle diameter of 147 microns with a standard deviation of 116 microns. After encapsulation, the octacosanol had an average particle size of 170 microns with a standard deviation of 74 microns.

We claim:

1. A comestible composition comprising
an alcohol having an average length of from about $C_{20}$–$C_{26}$ in a amount sufficient to reduce cholesterol in a vertebrae;
said alcohol encapsulated in a food grade acceptable cellulosic material selected from the group consisting of cellulose acetate, cellulose acetate butyrate, cellulose acetate phthalate, hydroxypropylcellulose, hydropropylmethylcellulose, methylcellulose, cellulose triacetate and ethylcellulose, wherein the weight ratio of alcohol to the food grade acceptable material is from about 1:4 to about 10:1 and the encapsulated alcohol has a diameter of less than about 200 microns.

2. The comestible composition of claim 1 wherein the comestible is selected from the group consisting of margarine, spreads, dressings, and oils.

3. The comestible composition of claim 1 wherein the comestible is aqueous based.

4. The comestible composition of claim 1 which additionally contains a second cholesterol reducing agent in an amount sufficient to reduce the cholesterol level in a human being.

5. The comestible composition of claim 4 wherein the second cholesterol reducing agent is selected from the group consisting of sterols, stanols, sterol esters, stanol esters and oryzanol.

6. A method for reducing cholesterol in a vertebrate comprising administering an effective amount of the comestible composition of claim 1.

* * * * *